US008651861B2

(12) United States Patent
Abel

(10) Patent No.: US 8,651,861 B2
(45) Date of Patent: Feb. 18, 2014

(54) SULCUS IMPRESSION TIP

(75) Inventor: Don E. Abel, Olney, IL (US)

(73) Assignee: DENTSPLY International Inc, York, PA (US)

( * ) Notice: Subject to any disclaimer, the term of this patent is extended or adjusted under 35 U.S.C. 154(b) by 30 days.

(21) Appl. No.: 13/065,020

(22) Filed: Mar. 11, 2011

(65) Prior Publication Data
US 2011/0223556 A1 Sep. 15, 2011

Related U.S. Application Data

(60) Provisional application No. 61/340,122, filed on Mar. 12, 2010.

(51) Int. Cl.
A61C 5/04 (2006.01)

(52) U.S. Cl.
USPC .......................................... 433/90

(58) Field of Classification Search
USPC ................ 433/87, 90, 141, 25, 80, 89, 217.1; 222/570, 566, 568, 575; 604/21, 117, 604/264, 218
See application file for complete search history.

(56) References Cited

U.S. PATENT DOCUMENTS

| | | | | |
|---|---|---|---|---|
| 3,654,502 A | * | 4/1972 | Carmona et al. | 433/119 |
| 4,315,743 A | * | 2/1982 | Brugirard | 433/90 |
| 4,442,977 A | * | 4/1984 | Beiswenger et al. | 239/332 |
| 5,022,859 A | * | 6/1991 | Oliva | 433/141 |
| 5,052,927 A | * | 10/1991 | Discko, Jr. | 433/90 |
| 5,336,088 A | * | 8/1994 | Discko, Jr. | 433/90 |
| 6,079,979 A | * | 6/2000 | Riitano | 433/81 |
| 6,311,869 B1 | * | 11/2001 | Horth et al. | 222/137 |
| 2003/0022131 A1 | * | 1/2003 | Kangasniemi et al. | 433/147 |
| 2009/0259143 A1 | * | 10/2009 | Bakhtyari-Nejad-Esfahani | 600/573 |

* cited by examiner

Primary Examiner — Heidi M Eide
Assistant Examiner — Justin O'Donnell
(74) Attorney, Agent, or Firm — Leana Levin; Douglas J. Hura; David A. Zdurne

(57) ABSTRACT

A sulcus impression tip for injecting dental impression material for making dental impressions. The tip includes a body having a gripping portion and a discharge tip having a bore there through which permits a friction fit with the outside diameter of needle cannula. The needle cannula extends approximately 2 millimeters past a distal end of the discharge tip. The body further defines an angle for holding the gripping portion to permit the discharge tip and needle cannula to be positioned for easy access in the oral cavity by the dentist. The discharge tip is sized and shaped to separate the gum from the tooth in the selected region so that the needle cannula is positioned to permit exact positioning for placement of the dental impression material along the sulcus.

11 Claims, 3 Drawing Sheets

SULCUS IMPRESSION TIP

CROSS REFERENCES TO RELATED APPLICATIONS

U.S. Provisional Application for Patent No. 61/340,122, filed Mar. 12, 2010, with title "Sulcus Impression Tip" which is hereby incorporated by reference. Applicant claims priority pursuant to 35 U.S.C. Par. 119(e)(i).

Statement as to rights to inventions made under federally sponsored research and development: Not Applicable

BACKGROUND OF THE INVENTION

1. Field of the Invention

The present invention relates in general to an instrument for ejecting material, and more particularly to an instrument useful in ejecting dental impression material for making dental impressions.

2. Brief Description of Prior Art

For a preparation of a dental prosthesis, an impression of the teeth and the part of the jaw adjacent to these teeth must be provided to the dental technician. Prior to this time, a dentist has usually completed preparation of the patient for taking the impression, which involves both cleaning the area and adequately exposing the tooth at or below the gum line, as necessary, for reception of the impression material. The groove defined between the tooth and gum in this region is usually referred to as the "sulcus". It is important that each concave and convex surface on which the impression material is to be placed be dry, because the impression material will not otherwise adhere. The presence of seepage and the physical characteristics of the impression material tend to introduce voids, bubbles and incompletely filled areas into the impression.

Different techniques have previously been employed for allowing the impression material to be properly applied.

To obtain clear access to the sulcus and the margin line which the casting base is to follow, a packing material or gingival retraction cord is often used to separate the gum from the tooth in this region. However, this technique is time-consuming and often involves traumatizing of the gingival tissues, frequently causing bleeding. Such bleeding complicates the impression taken, often requiring the dentist to discontinue further work until the bleeding has stopped. Further, seepage usually begins as soon as the packing material is taken out, or can be continuous if no packing is used. As stated, impression material will not adhere to wet surface but instead, slips to another region.

The prior art techniques known are very time-consuming causing frustration to the dentist, and often involve traumatizing of the gingival tissues, frequently causing bleeding.

It should be kept in mind that an accurate impression must be taken as expeditiously as possible, for the benefit of both the patient and the dentist. To accomplish this a versatile instrument capable of being used in different ways to overcome different problems is highly desirable but is not heretofore been available.

An object of the present invention is to provide an applicator particularly useful in making dental impressions which reduces or avoids the above drawbacks.

SUMMARY OF THE INVENTION

A sulcus impression tip useful for use in injecting dental impression material for making dental impressions. The apparatus generally comprises a body having a gripping portion and a discharge tip. Within the discharge tip is a needle cannula. A flare or flange that receives and holds the dental impression material is in fluid communication with the needle cannula and is secured in the interior surface of the gripping portion. The discharge tip has a bore there through which permits a friction fit with the outside diameter of needle cannula. The length of the needle cannula is approximately longer than the length of the discharge tip such that the needle cannula extends approximately two millimeters past the distal end of the discharge tip. The body and needle cannula in connection with the flare or flange define an angle such that when the dentist is holding the gripping portion, the angle permits the discharge tip and needle cannula to be positioned for easy access in the oral cavity by the dentist. The discharge tip is sized and shaped to effectively separate the gum from the tooth in the selected region so that the needle cannula is positioned to permit exact positioning for placement of the dental impression material along the sulcus.

DESCRIPTION OF THE PREFERRED EMBODIMENT

Figure 1:
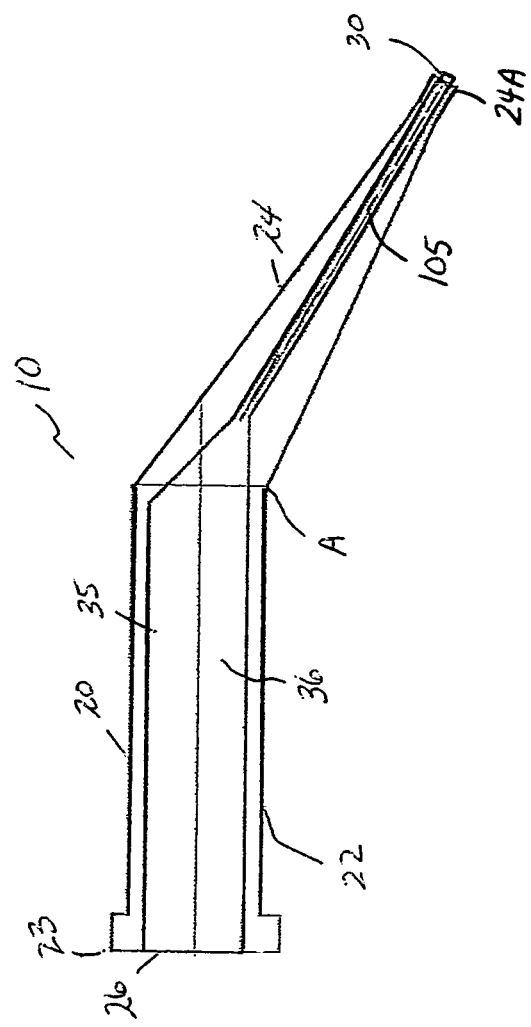
FIG. 1 is a top perspective view of the present invention, a sulcus impression tip.
Figure 2:
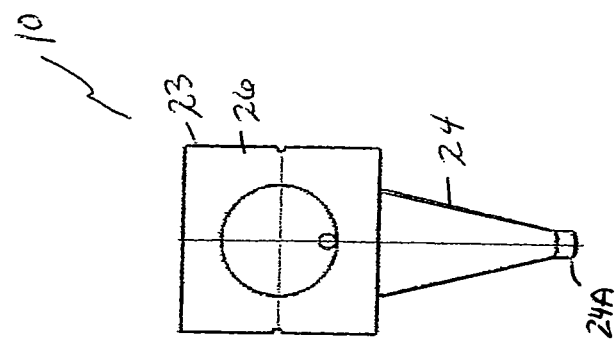
FIG. 2 is an end view of the sulcus impression tip of FIG. 1

The apparatus of the present invention is directed to an applicator useful for use in injecting dental impression material for making dental impressions. The apparatus holds the flowable dental impression material and enables the dentist to precisely place the impression material into the sulcus area around the prepared tooth in the fabrication of dental prosthesis. Unlike the prior art, the sulcus impression tip of the present invention permits the use of only one impression material viscosity which therefore eliminates the necessity of first using light bodied impression material as is known. Further, and unlike the prior art, the tip of the present invention does not rotate upon contact. Known applicators, which do rotate, prevent precise control in the placement of the impression material. As will be described, the sulcus impression tip as disclosed consists of components configured and correlated with respect to each other so as to attain the desired objective.

Referring to the drawings, the sulcus impression tip, indicated generally at 10, comprises a body 20 having a gripping portion 22 at one end and a discharge tip 24 at the opposite end. The discharge tip 24 is formed as a part of or integrally with the gripping portion 22. Within the discharge tip 24 is a needle cannula 30. An adapter end 23 of the gripping portion 22 is open and includes square fitting end 26 to which a pressure source such as a plunger assembly or compressed air line may be connected. If used, the air line is connected to the usual compressed air source provided in a dentist's office. The square shape of the adapter end 23 prevents rotation of the body 20. Normally, syringe ends are round and allow rotation but placing material in the sulcus works better if the body can't rotate relative to the syringe.

As illustrated, the discharge tip 24 has a relatively long solid portion with a bore there through. Through this bore is placed the needle cannula 30. The needle cannula 30 comprises a metal needle having a selected gauge size bore there through. The body 20 defines a flare or flange 35 inside. The flange 35 is of the shape of a funnel having sides that are oblique to the longitudinal access of the discharge tip 24 and needle cannula 30.

This discharge tip 24 has a bore there through which permits a friction fit with the outside diameter of needle cannula 30. The length of the discharge tip 24 and bore therein is sufficiently long to provide support for the needle cannula 30. As further illustrated, the length of the needle cannula 30 is approximately longer than the length of the discharge tip 24 such that the needle cannula 30 extends approximately two millimeters past the distal end of the discharge tip 24.

The body 20 is preferably made of an inexpensive plastic that is relatively soft in order to reduce the cost and complexity of manufacturing.

As further illustrated, the body 20, and needle cannula 30 in connection with the flare or flange 35, includes an angle designated as A. In application, when the dentist is holding the gripping portion 22, the angle A permits the discharge tip 24 and needle cannula 30 to be positioned for easy access in the oral cavity by the dentist. The angle A further prevents the needle cannula 30 from rotating within the body 20. Again, this non-rotation feature is distinguishable over the prior art.

Figure 3:
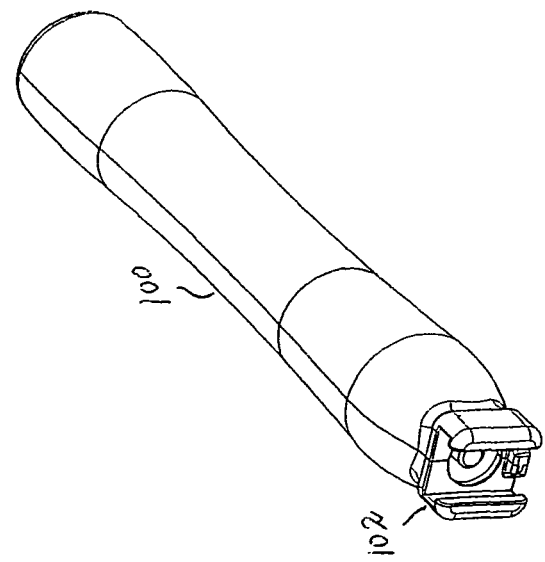
FIG. 3 shows a view of a pressure source.

FIG. 3 shows a view of a pressure supply source such as a source of compressed air or syringe plunger 100 as described in U.S. Pat. Pub. No. 20100285425. The syringe plunger 100 includes a groove 102 sized to allow the square end 26 of the body 20 to slidingly fit into the groove 102 such that the walls of the groove 102 prevent the body 20 from rotating relative to the syringe plunger 100. This improves the user's ability to apply material along the sulcus.

The flange 35 includes a chamber 36 that receives and holds the dental impression material and, the chamber 36 is in fluid communication with the needle cannula 30. The impression material disclosed as a sulcus can then maintain the separation between the gum and tooth once the discharge tip 24 is removed and until the impression is taken. The chamber 36 generally has a cylindrical shape and central axis and is adapted to receive a pressure source such as a syringe plunger 100. In application, once the dental impression material is placed within the chamber 36 of the present invention, the syringe plunger 100 assembly is attached to the distal end 23 of the gripping portion 22. The dental impression material can then be extruded as needed by the dentist. The discharge tip 24 has a tapered configuration and is sized and shaped to effectively separate the gum from the tooth in the selected region so that the needle cannula 30 is positioned and extends past the end of the discharge tip 24 to permit exact positioning of the needle cannula 30 for placement of the dental impression material 105 along the sulcus. More particularly, the discharge tip 24 includes a distal end 24A having a width larger than the outside diameter of the needle cannula 30. The distal end 24A surrounds the needle cannula 30. The distal end 24A preferably has a width of 1.5 millimeters. The needle cannula 30 preferably has an outside diameter of 1.067 millimeters. The impression material disposed in the sulcus can then maintain the separation between the gum and tooth once the discharge tip 24 is removed and until the impression is taken.

Although the above description above contains many specificities, these should not be construed as limiting the scope of the invention but as merely providing illustrations of some of the presently preferred embodiments of this invention. As such, it is to be understood that the present invention is not limited to the embodiments described above, but encompasses any and all embodiments within the scope of the claims.

It would be obvious to those skilled in the art that modifications may be made to the embodiments described above without departing from the scope of the present invention. Thus the scope of the invention should be determined by the appended claims in the formal application and their legal equivalents, rather than by the examples given.

I claim:

1. A sulcus impression tip comprising:
   a body having a gripping portion and a discharge tip,
   wherein the discharge tip has an external tapered portion and an external straight portion having a distal end, wherein said external tapered portion has a first end and a second end, and wherein a first end of said straight portion extends from said second end of said external tapered portion, said first end of said straight portion opposite said distal end, wherein the discharge tip has a bore there through having an internal continuously tapered portion and an internal straight portion, the internal straight portion extending through both the external straight and tapered portions of the discharge tip, an outside diameter of a needle cannula is friction fit within the bore, wherein the length of the needle cannula is approximately longer than the length of the discharge tip such that a first end of the needle cannula is positioned within the internal straight portion of the bore, and a second end of the needle cannula extends a distance past the distal end,
   a flange in fluid communication with said needle cannula, and said flange disposed within said gripping portion and having a chamber for receipt of dental impression material,
   wherein said body defines an angle such that when a dentist is holding the gripping portion, the angle permits the discharge tip and needle cannula to be positioned for easy access in the oral cavity by the dentist,
   wherein said body includes a square end for sliding into a groove of a pressure supply source, and wherein said distal end having a width greater than an outside diameter of said needle cannula such that said straight portion is sized and shaped for separating the gum from the tooth in the selected region so that the needle cannula is positioned to permit exact positioning for placement of the dental impression material along the sulcus.

2. The sulcus impression tip as recited in claim 1, wherein the angle is an angle between the body and the discharge tip and the angle is approximately thirty degrees.

3. A sulcus impression tip comprising:
   a body having a gripping portion and a discharge tip,
   wherein the discharge tip has an external tapered portion and an external straight portion having a distal end, wherein said external tapered portion has a first end and a second end, wherein a first end of said straight portion extends from said second end of said external tapered portion, said first end of said straight portion opposite said distal end, wherein the discharge tip has a bore there through having an internal continuously tapered portion and an internal straight portion, the internal straight portion extending through both the external straight and tapered portions of the discharge tip, an outside diameter of a needle cannula is friction fit within the bore, wherein the length of the cannula is approximately longer than the length of the discharge tip such that a first end of the cannula is positioned within the internal straight portion of the bore, and a second end of the cannula extends a distance past said distal end, a flange in fluid communication with said cannula, and said flange disposed within said gripping portion and having a chamber for receipt of dental impression material, wherein said body defines an angle such that when a dentist is holding the gripping portion, the angle permits the discharge tip and cannula to be positioned for easy access in the oral cavity by the dentist, wherein said distal end surrounds said cannula and has a width larger than an outside diameter of said cannula such that said straight portion is sized and shaped to separate the gum from the tooth in the selected region so that the cannula is positioned to permit exact positioning for placement of the dental impression material along the sulcus.

4. The sulcus impression tip as recited in claim 3, wherein said body includes a pressure source adapter having a square shape for connecting to a pressure source that prevents rotation of the body relative to the pressure source.

5. The sulcus impression tip as recited in claim 4, wherein said cannula is a metal needle cannula and wherein said metal needle cannula extends beyond said discharge tip.

6. The sulcus impression tip as recited in claim 4, wherein the angle is an angle between the body and the discharge tip and the angle is approximately thirty degrees.

7. A sulcus impression tip comprising:

a body having a gripping portion and a discharge tip, wherein the discharge tip includes an external tapered portion, an external straight portion having a distal end, wherein said external tapered portion has a first end and a second end, and wherein a first end of said straight portion extends from said second end of said external tapered portion, said first end of said straight portion opposite said distal end, wherein the discharge tip has a bore there through having an internal continuously tapered portion and an internal straight portion, the internal straight portion extending through both the external straight and tapered portions of the discharge tip, an outside diameter of a needle cannula is friction fit within the bore, wherein the length of the needle cannula is approximately longer than the length of the discharge tip such that a first end of the needle cannula is positioned within the internal straight portion of the bore, and a second end of the needle cannula extends a distance past said distal end, a flange in fluid communication with said needle cannula, and said flange disposed within said gripping portion and having a chamber for receipt of dental impression material, wherein said body defines an angle such that when a dentist is holding the gripping portion, the angle permits the discharge tip and needle cannula to be positioned for easy access in the oral cavity by the dentist, wherein said body includes a square end for sliding attachment to a pressure supply source, and wherein said distal end of said discharge tip having a width sized and shaped for separating the gum from the tooth in the selected region so that the needle cannula is positioned to permit exact positioning for placement of the dental impression material along the sulcus.

8. The sulcus impression tip as recited in claim 7, wherein said needle cannula is metal.

9. The sulcus impression tip as recited in claim 8, wherein the angle is an angle between the body and the discharge tip and the angle is approximately thirty degrees.

10. The sulcus impression tip as recited in claim 9, wherein the width of said distal end is 1.5 millimeters.

11. The sulcus impression tip as recited in claim 10, wherein an outside diameter of said needle cannula is 1.067 millimeters.

\* \* \* \* \*